(12) United States Patent
Grahek et al.

(10) Patent No.: US 6,695,969 B1
(45) Date of Patent: Feb. 24, 2004

(54) PROCESS FOR OBTAINING HMG-COA REDUCTASE INHIBITORS OF HIGH PURITY

(75) Inventors: Rok Grahek, Kranj (SI); Dusan Milivojevic, Ljubljana (SI); Andrej Bastarda, Vrhnika (SI)

(73) Assignee: LEK Pharmaceuticals d.d., Ljubljana (SI)

( * ) Notice: Subject to any disclaimer, the term of this patent is extended or adjusted under 35 U.S.C. 154(b) by 0 days.

(21) Appl. No.: 09/720,952

(22) PCT Filed: Sep. 17, 1999

(86) PCT No.: PCT/IB99/01553

§ 371 (c)(1),
(2), (4) Date: Jan. 3, 2000

(87) PCT Pub. No.: WO00/17182

PCT Pub. Date: Mar. 30, 2000

(30) Foreign Application Priority Data

Sep. 18, 1998 (SI) ................................................ P980241

(51) Int. Cl.$^7$ .............................................. B01D 15/08
(52) U.S. Cl. ..................... 210/656; 210/198.2; 530/344; 549/292
(58) Field of Search ............................. 210/656, 198.2; 530/344; 549/292

(56) References Cited

U.S. PATENT DOCUMENTS

| | | | | |
|---|---|---|---|---|
| 4,231,938 A | | 11/1980 | Monaghan | 260/343.5 |
| 5,043,423 A | | 8/1991 | Viscomi et al. | 530/344 |
| 5,202,029 A | * | 4/1993 | Haytko et al. | 210/656 |
| 5,420,024 A | * | 5/1995 | Carta et al. | 435/125 |
| 5,427,686 A | | 6/1995 | Asher | 210/635 |
| 6,268,186 B1 | * | 7/2001 | Sibeijn et al. | 435/125 |

FOREIGN PATENT DOCUMENTS

| | | | |
|---|---|---|---|
| EP | 0 416 416 A1 | 3/1991 | C07K/1/14 |
| WO | WO 92/16276 | 10/1992 | B01D/15/08 |

OTHER PUBLICATIONS

Horvath, C (1985): J. Chromatography Library, vol 32, 179–203.*

Felinger et al., Optimization of the experimental conditions and the column design partners in displacement chromatography, Journal of Chromatography vol. 609, pp. 35–47, (1992).

Frenz, Frontiers of Biopolymer Purification: Displacement Chromatography, LC–GC International, Vol 5, pp. 18–21, (1992).

Gu et al., Displacement Effect in Multicomponent Chromatography, AIChE Journal, vol. 36, pp. 1156–1162(1990).

Subramanian et al., Displacement Chromatography of Biomolecules, Journal of Chromatography, vol. 439, pp. 341–351, (1988).

Cramer et al., Tandem use of Carboxypeptidase Y. Reactor and Displacement Chromatography for Peptide Synthesis, Journal of Chromatography, vol. 394, pp. 305–314 (1987).

* cited by examiner

Primary Examiner—Alan L. Rotman
Assistant Examiner—Golam M M Shameem
(74) Attorney, Agent, or Firm—Bromberg & Sunstein LLP

(57) ABSTRACT

Lovastatin, pravastatin, simvastatin, mevastatin, atorvastatin, and derivatives and analogs thereof are known as HMG-CoA reductase inhibitors and are used as and antihypercholesterolemic agents. The majority of them are produced by fermentation using microorganisms of different species identified as species belonging to Aspergilus, Monascus, Nocardia, Amycolatopsis, Mucor or Penicilium genus, some are obtained by treating the fermentation products using the method of chemical synthesis or they are the products of total chemical synthesis. The purity of the active ingredient is an important factor for manufacturing the safe and effective pharmaceutical, especially if the pharmaceutical product must be taken on a longer term basis in the treatment or prevention of high plasma cholesterol. The accumulation of the impurities from the pharmaceuticals of lower purity may cause many side effects during the medical treatment. The present invention relates to a new industrial process for the isolation of HMG-CoA reductase inhibitors using so-called displacement chromatography. Use of the invention enables to obtain HMG-CoA reductase inhibitors of high purity, with high yields, lower production costs and suitable ecological balance.

26 Claims, No Drawings

PROCESS FOR OBTAINING HMG-COA REDUCTASE INHIBITORS OF HIGH PURITY

This application is a 371 of PCT/1B99/01553 Sep. 17, 1999.

TECHNICAL FIELD

Lovastatin, pravastatin, simvastatin, mevastatin, atorvastatin and derivatives and analogs thereof are known as HMG-CoA reductase inhibitors and are used as antihypercholesterolemic agents. The majority of them are produced by fermentation using microorganisms of different species identified as species belonging to Aspergillus, Monascus, Nocardia, Amycoiatopsis, Mucor or Penicillium genus, some are obtained by treating the fermentation products using the method of chemical synthesis or they are the products of total chemical synthesis.

The purity of the active ingredient is an important factor for manufacturing the safe and effective pharmaceutical, especially if the pharmaceutical product must be taken on a longer term basis in the treatment or prevention of high plasma cholesterol. The accumulation of the impurities from the pharmaceuticals of lower purity may cause many side effects during the medical treatment.

The present invention relates to a new industrial process for the isolation of HMG-CoA reductase inhibitors using so-called displacement chromatography. Use of the invention enables to obtain HMG-CoA reductase inhibitors of high purity, with high yields, lower production costs and suitable ecological balance.

Prior Art

The processes for the isolation and purification of antihypercholesterolemic agents disclosed in the earlier patents include a variety of combinations of extraction, chromatography, lactonisation and crystallisation methods. The purity of the final product obtained by these procedures comply with the USP standards but the yields of the desired product are relatively low. In addition, they require both large amounts of organic solvents and the large equipment suited for these quantities.

The isolation process disclosed in WO 92/16276 provides the solution for obtaining HMG-CoA reductase inhibitors of purity greater than 99.5% with the use of industrial RPLC (high performance liquid chromatography) equipment. According to WO 92/16276 the crude HMG-CoA reductase inhibitor, with a purity of ≧85%, is dissolved in an organic solvent or in a solution of organic solvent and water. The mixture is then buffered to a pH between 2 and 9 and placed on the HPLC column. After the HMG-CoA reductase inhibitor peak of interest is collected, a portion of solvent is removed and the water is added or alternatively two-thirds of the solvent mixture are removed and the HMG-CoA reductase inhibitor is crystallised. At the end, the purity of the product obtained by this process is at least 99.5% with the yield of around 90%.

The method disclosed in WO 92/16276 enables obtaining of HMG-CoA reductase inhibitors of high purity, with relatively high yields, the disadvantage of the method over the conventional chromatography columns are relatively small quantities of the substance loaded per HPLC column. Small samples to be fed into the column are also related with increased number of repetitions of the isolation operations in order to obtain sufficient quantities of the desired substance, and consequently large amount of the solvents used resulting in higher production costs.

Displacement chromatography method, the basis of the present invention, does not substantially differ from previously used chromatography methods.

Displacement chromatography is based on competition of the components of the sample fed into the column for active sites on the stationary phase. Individual components of the sample displace one another like a train, the displacer, having the very high affinity for the stationary phase and travelling behind the fed sample along the column, drives the separation of the sample components into onecompartment zones which move at the same velocity as the displacer. Concentrating of individual components is carried out simultaneously with the purification.

The principle of displacement chromatography method is relatively old as it has been known since 1943 but it was introduced into practice as late as 1981 because of the lack of efficient columns (Cs. Horvath et al., J. Chromatogr., 215 (1981) 295; J. Chromatogr., 330 (1985) 1; J. Chromatogr., 440 (1988) 157). These papers, introduced herein by way of reference, describe the analytic and preparative separation and purification of biologically active peptides and polymyxin antibiotics (polypeptides) using reversed-phase high performance liquid chromatography columns in the displacement mode. For polymyxins octadecyl silica gel columns 250×4.6 mm, particle size 5 $\mu$m, 10% acetonitrile in water as the mobile phase and different tetraalkylammonium halogenides as the displacer were used.

In recent investigations in the field of displacement chromatography (S. M. Cramer et al., Enzyme Microb. Technol., 11 (1989) 74; Prep. Chromatogr., 1 (1988) 29; J. Chromatogr., 394 (1987) 305; J. Chromatogr., 439 (1988) 341; J. Chromatogr., 454 (1988) 1 (theoretic optimisation)); A. Felinger et al., J. Chromatogr., 609 (1992) 35 (theoretic optimisation), all papers being introduced herein by way of reference) similar columns were used; the mobile phase was methanol in the phosphate buffer, the displacer was 2-(2-t-butoxyethoxy)ethanol (BEE) in acetonitrile and sodium acetate. Different peptides, proteins and cephalosporin C antibiotic were used as the samples.

U.S. Pat. No. 5,043,423 (Aug. 27, 1991) and EP 416.416, respectively, describe the method for purifying certain low molecular (below 1000 daltons) peptides (in particular, tuftsin and synthetic derivatives thereof) with displacement ion-exchange chromatography where the stationary phase used is cationic-exchange resin, the transporter solvent is water or dilute solutions of a variety of strong acids, and the displacer used is triethylenetetraammonuim salt in different concentrations. In U.S. patent application Ser. No. 08/875, 422, yet unpublished, the use of displacement chromatography for the isolation and purification of vancomycin is described.

Technical Solution

It is sometimes difficult to obtain the active substance of high purity in a large scale as many technologies applicable to a laboratory scale are not sufficiently economical in large scale production operations to justify use thereof or do not meet the environmental criteria. The above facts compel the industry to search for new technologies that will provide both the high-quality product and the economically and ecologically acceptable production.

The present invention has solved the drawbacks of the processes known from the older patents and other literature as it enables to obtain the pure HMG-CoA reductase inhibitors and, additionally, the purifying process per se is not time-consuming providing high yields, using small amounts of solvents. The process is nature friendly; in addition, it is not demanding in terms of space and energy thus enabling an economical large scale production.

Description of the invention

The present invention provides a process for the purification of HMG-CoA reductase inhibitors employing displacement chromatography. That is, at least one of the steps in the process of the purification of crude HMG-CoA reductase inhibitor includes displacement chromatography.

The HMG-CoA reductase inhibitor to be purified is, for example, selected from the group consisting of mevastatin, pravastatin, lovastatin, simvastatin, fluvastatin and atorvastatin. The selected inhibitor may be in the lactone form or in the form of the acid or the salt thereof for being purified by means of displacement chromatography.

The displacement chromatography being characteristic for the process of the present invention preferably includes the following steps:

a) conditioning a chromatography column with an appropriate mobile phase, b) feeding the crude HMG-CoA reductase inhibitor dissolved in the mobile phase, c) introducing the displacer for displacing the HMG-CoA reductase inhibitor from the column, and d) obtaining the purified HMG-CoA reductase inhibitor.

The purified HMG-CoA reductase inhibitor is preferably obtained by d1) collecting the fractions and d2) analyzing the fractions with analytical HPLC and pooling the fractions depending on the quality of purity.

After the purified HMG-CoA reductase inhibitor has been obtained, the chromatography column may be regenerated by washing of the column with alcohol/water mixture to elute the displacer.

HMG-CoA reductase inhibitors obtained in the herein-described manner are then isolated from the mobile phase according to the methods already known from the state of prior art, for example by lyophilisation or, prefarably, by crystallization to obtain the lactone form, the acid form or the salt form (preferably alkaline or earth alkaline salts) thereof.

The fractions containing a considerable percentage of HMG-CoA reductase inhibitors, in addition to impurities, may be re-subjected to the process resulting in the total yield exceeding 95%.

The stationary phase used is a reverse phase where natural (silica gel with alkyl chains of a different length) or synthetic (C-18 or C-8 organic) stationary phases are suitable. Preferably, a synthetic cross-linked polymer matrix of styrene and divinylbenzene is used. The particle size of the stationary phase is suitably from 3 to 20 $\mu$m, preferably between 7 and 15 $\mu$m.

The mobile phase used is preferably selected from water, acetonitrile/water solution and aqueous solutions of lower (preferably $C_1$–$C_4$) alcohols, buffered dilute solutions of organic, halogenated organic or inorganic acids, e.g. formic, acetic, propionic, hydrochloric, boric, phosphoric, carbonic or sulphuric acids with cations of alkaline metals, with ammonia or with amines. Water and aqueous solutions with acetonitrile and especially with methanol or ethanol are particularly preferred, and the content of the organic solvent in the aqueous solutions preferably is 80% or below, more preferably 45% or below and particularly 30% or below. Since toxic methanol in the mobile phase may be replaced by less toxic ethanol, or may be at least partially replaced by water with good results, removal of waste solvents is simpler, therefore, the present invention is a marked improvement compared to the state of prior art judging from the ecological aspect.

The pH of the mobile phase used is preferably between 4.5 and 10.5, more preferably between 6.5 and 8, and particularly around 7. The flow rate of the mobile phase through the column is suitably adjusted to lie between 1.5 and 30 ml/(min cm$^2$), preferably between 3 and 15 ml/(min cm$^2$). At the time when the displacer is introduced into the chromatography column by being mixed with the mobile phase, the flow rate is preferably adjusted to lie between 1.5 and 15 ml/(min cm$^2$) and particularly between 3 and 10 ml/(min cm$^2$), because higher flow rates cause the dilution of the samples to be collected, and also the separation becomes worse.

The displacer suitably is a compound having an amphiphilic structure, such as surfactants, detergents and the like. Examples of the displacer are long chain alcohols, long chain carboxylic acids, long chain alkyl ammonium salts, aromatic dicarboxylic acid esters, oxo- and dioxo-alcohols, polyalkylene polyglycol ethers such as diethylene glycol mono- (or di-)alkylethers, polyaryl or polyalkylene polyaryl ethers such as Tritone® X-100, etc. The aforementioned "long chain" means an alkyl chain having at least a $C_4$-chain, preferably at least a $C_{10}$-chain and more preferably at least a $C_{14}$-chain or longer.

The concentration of the displacer in the mobile phase is suitably adjusted to be from 1 to 35%, preferably from 2 to 20% and particularly from 7 to 14%.

In the preferred embodiment of controlling the quality of purity in the individual fractions eluted from the chromatography column, an analytical HPLC method directed to the HMG-CoA reductase inhibitors to be analyzed may be carried out as described in the following.

The sample to be analysed is diluted 100 times with the mobile phase containing 20 mM aqueous NH$_4$HCO$_3$ solution with acetonitrile (the proportion of acetonitrile is adjusted such that the retention factor of the analyte is between 5 and 10). 10 $\mu$l of this sample is placed on Hypersil ODS column (Hypersil, the United Kingdom, particle size 3 $\mu$m, column size 50×4.6 mm) for high performance liquid chromatography. The column is washed with the mobile phase at the flow rate of 2 ml/min. Absorbance is measured at 235 nm. HPLC purity of the sample is calculated from the ratio between the areas of individual peaks in the chromatogram.

After completed chromatography the stationary phase is preferably regenerated, for example using the mobile phase with 20 to 100% aqueous solution of lower alcohol.

The invention is illustrated but in no way limited by the following examples.

EXAMPLES

Example 1

Crude sodium salt of pravastatin (1.0 g, HPLC purity 88%, assay 85%) was dissolved in 10 ml of the mobile phase A (distilled water), pH was adjusted to 7 with 0.2M aqueous NaOH solution and filtered. The column was equilibrated with mobile phase A. The sample obtained in the above-described manner was fed onto the Grom-Sil 120-ODS HE column (Grom Analytic+HPLC GmbH, Germany), particle size 11 $\mu$m, column size 250×10 mm. The column was washed with the mobile phase B containing 7% of diethyleneglycol monobutylether in mobile phase A at the flow rate of 4.5 ml/min. Absorbance was measured at 260 nm, and the 0.5 ml fractions were collected with an initial increase in the absorbance. When the signal decreased the column was washed with 25 ml of 70% methanol. The obtained fractions were analyzed by the herein above-described HPLC analytical method. The fractions with a purity≧99.5% were pooled. In the pooled fractions (7 ml) the HPLC purity was 99.8%.

Example 2

Crude sodium salt of pravastatin (0.4 g, HPLC purity 88%, assay 85%) was dissolved in 5 ml of the mobile phase A (distilled water), pH was adjusted to 7 with 0.2M aqueous NaOH solution and filtered. The column was equilibrated with mobile phase A. The sample obtained in the above-described manner was fed onto the Kromasil 100 C-18 column (EKA Chemicals AB, Sweden), particle size 10 $\mu$m, column size 200×10 mm. The column was washed with the mobile phase B containing 7% of Triton X-100 in mobile phase A at the flow rate of 1 ml/min. Absorbance was measured at 260 nm, and the 0.5 ml fractions were collected with an initial increase in the absorbance. The obtained fractions were analysed by the above described HPLC analytical method. The fractions with a purity≧99.5% were pooled. In the pooled fractions (3 ml) the HPLC purity was 99.7%.

Example 3

0.6 g of the crude sodium salt of pravastatin was dissolved in 5 ml of distilled water. The protocol described in Example 1 was used with the exception of the mobile phase used (30% aqueous methanol solution) and the pooled fractions with a HPLC purity of 99.8% were obtained.

Example 4

The method described in Example 3 was repeated wherein the concentration of the displacer in the mobile phase was 14%. In the fractions pooled, according to the criterion described in Example 1, HPLC purity was 99.8%.

Example 5

Pravastatin lacton (0.4 g, HPLC purity 85%) was dissolved in 33 ml of the mobil phase A containing 45% methanol. The column was equilibrated with mobile phase A. The sample obtained in the above-described manner was fed onto the Grom-Sil 120-ODS HE column (Grom Analytic+HPLC GmbH, Germany), particle size 11 $\mu$m, column size 250×10 mm. The column was washed with the mobile phase B containing 2% of diethyleneglycoldibutylether in mobile phase A at the flow rate of 4.5 ml/min. Absorbance was measured at 260 nm, and the 1 ml fractions were collected with an initial increase in the absorbance. When the signal decreased the column was washed with 25 ml of 70% methanol.

The fractions with a purity≧99.5% were pooled. In the pooled fractions the HPLC purity was 99.7%.

Example 6

Pravastatin lacton (0.3 g, HPLC purity 85%) was dissolved in 80 ml of the mobil phase A containing 30% methanol. The column was equilibrated with mobile phase A. The sample obtained in the above-described manner was fed onto the Licrosphere RP 18 column, particle size 12 $\mu$m, column size 200×10 mm. The column was washed with the mobile phase B containing 5% of diethyleneglycolmono-n-hexylether in mobile phase A at the flow rate of 4.5 ml/min. Absorbance was measured at 235 nm, and the 1 ml fractions were collected with an initial increase in the absorbance. When the signal decreased the column was washed with 25 ml of 90% methanol. The obtained fractions were analysed by the above described HPLC analytical method.

The fractions with a purity≧99.5% were pooled. In the pooled fractions the HPLC purity was 99.8%.

Example 7

Pravastatin lacton (0.3 g, HPLC purity 85%) was dissolved in 25 ml of the mobil phase A containing 35% acetonitrile. The column was equilibrated with mobile phase A. The sample obtained in the above-described manner was fed onto the Licrosphere RP 18 column, particle size 12 $\mu$m, column size 200×10 mm. The column was washed with the mobile phase B containing 1% of diethyleneglycoldibutylether in mobile phase A at the flow rate of 4.5 ml/min. Absorbance was measured at 235 nm, and the 1 ml fractions were collected with an initial increase in the absorbance. When the signal decreased the column was washed with 25 ml of 90% methanol. The obtained fractions were analysed by the above described HPLC analytical method.

The fractions with a purity≧99.5% were pooled. In the pooled fractions the HPLC purity was 99.8%.

Example 8

The method described in Example 7 was repeated wherein the mobile phase B was 0.85% diethylphthalat in the mobile phase A.

The fractions with a purity≧99.5% were pooled. In the pooled fractions the HPLC purity was 99.8%.

Example 9

Simvastatin lacton (0.42 g, HPLC purity 87%) was dissolved in 6 ml of the 66% acetonitrile and hydrolysed with 1.2 mmol of sodium hydroxide. Acetonitrile was removed and pH was adjusted to 7 with diluted $H_3PO_4$. The column was equilibrated with mobile phase A containing 14% of methanol. The sample obtained in the above-described manner was fed onto the Grom-Sil 120-ODS HE column (Grom Analytic+HPLC GmbH, Germany), particle size 11 $\mu$m, column size 250×10 mm. The column was washed with the mobile phase B containing 6.7% of diethyleneglycolmono-n-hexylether in mobile phase A at the flow rate of 4.5 ml/min. Absorbance was measured at 260 nm, and the 0.5 ml fractions were collected with an initial increase in the absorbance. When the signal decreased the column was washed with 25 ml of methanol.

The fractions with a purity≧99.5% were pooled. In the pooled fractions the HPLC purity was 99.8%.

Example 10

Simvastatin lacton (0.5 g, HPLC purity 87%) was dissolved in 20 ml of the mobile phase containing 70% of methanol. The column was equilibrated with mobile phase A. The sample obtained in the above-described manner was fed onto the Grom-Sil 120-ODS HE column (Grom Analytic+HPLC GmbH, Germany), particle size 11 $\mu$m, column size 250×10 mm. The column was washed with the mobile phase B containing 3% of decanoic acid in mobile phase A at the flow rate of 4.5 ml/min. Absorbance was measured at 260 nm, and the 0.75 ml fractions were collected with an initial increase in the absorbance. When the signal decreased the column was washed with 25 ml of methanol. The obtained fractions were analyzed by the herein above described method. The fractions with a purity≧99.5% were pooled. In the pooled fractions the HPLC purity was 99.7%.

Example 11

Simvastatin lacton (0.5 g, HPLC purity 87%) was dissolved in 20 ml of the mobile phase containing of 60% acetonitrile. The column was equilibrated with mobile phase A. The sample obtained in the above-described manner was fed onto the Grom-Sil 120-ODS HE column (Grom Analytic+HPLC GmbH, Germany), particle size 11 μm, column size 250×10 mm. The column was washed with the mobile phase B containing 2% of tetrakis(decyl)amonium bromide in mobile phase A at the flow rate of 4.5 ml/min. Absorbance was measured at 260 nm, and the 1 ml fractions were collected with an initial increase in the absorbance. When the signal decreased the column was washed with 25 ml of methanol.

The fractions with a purity>99.5% were pooled. In the pooled fractions the HPLC purity was 99.8%.

Example 12

Lovastatin lacton (0.5 g, HPLC purity 87%) was dissolved in 60 ml of the 75% methanol. The column was equilibrated with mobile phase A containing 70% of methanol. The sample obtained in the above-described manner was fed onto the Grom-Sil 120-ODS HE column (Grom Analytic+HPLC GmbH, Germany), particle size 11 μm, column size 250×10 mm. The column was washed with the mobile phase B containing 70% of methanol and 4.5% of decanoic acid in mobile phase A at the flow rate of 6 ml/min. Absorbance was measured at 260 nm, and the 1 ml fractions were collected with an initial increase in the absorbance. When the signal decreased the column was washed with 25 ml of methanol.

The obtained fractions were analysed by the above described HPLC analytical method.

The fractions with a purity>99.5% were pooled. In the pooled fractions the HPLC purity was 99.9%.

Example 13

Lovastatin lacton (0.42 g, HPLC purity 87%) was dissolved in 8 ml of the 50% acetonitrile and hydrolysed with 1.5 mmol of sodium hydroxide. Acetonitrile was removed and pH was adjusted to 7 with diluted $H_3PO_4$. The column was equilibrated with mobile phase A containing 14% of methanol. The sample obtained in the above-described manner was fed onto the Grom-Sil 120-ODS HE column (Grom Analytic+HPLC GmbH, Germany), particle size 11 μm, column size 250×10 mm. The column was washed with the mobile phase B containing 6.7% of diethyleneglycolmono-n-hexylether in mobile phase A at the flow rate of 1 ml/min. Absorbance was measured at 260 nm, and the 0.25 ml it fractions were collected with an initial increase in the absorbance. When the signal decreased the column was washed with 25 ml of methanol.

The obtained fractions were analysed by the method described in Example 9. The fractions with a purity≧99.5% were pooled. In the pooled fractions the HPLC purity was 99.8%.

Example 14

Mevastatin lacton (0.5 g, HPLC purity 85%) was dissolved in 150 ml of the mobile phase A containing 70% of methanol. The column was equilibrated with mobile phase A. The sample obtained in the above-described manner was fed onto the Grom-Sil 120-ODS HE column (Grom Analytic+HPLC GmbH, Germany), particle size 11 μm, column size 250×10 mm. The column was washed with the mobile phase B containing 4.5% of decanoic acid in mobile phase A at the flow rate of 6 ml/min. Absorbance was measured at 260 nm, and the 1 ml fractions were collected with an initial increase in the absorbance. When the signal decreased the column was washed with 25 ml of methanol.

The obtained fractions were analysed by the above described HPLC analytical method.

The fractions with a purity>99.5% were pooled. In the pooled fractions the HPLC purity was 99.8%.

What is claimed is:

1. A process for obtaining a HMG-CoA reductase inhibitor comprising one of the steps in the process of the purification of a crude HMG-CoA reductase inhibitor which consists of displacement chromatography and involves using a displacer for displacing the HMG-CoA reductase inhibitor.

2. A process according to claim 1, wherein the HMG-CoA reductase inhibitor is selected from the group consisting of mevastatin, pravastatin, lovastatin, simvastatin, fluvastatin or atorvastatin.

3. A process according to claim 1, wherein the HMG-CoA reductase inhibitor has a lactone form or is in the form of the acid or the salt thereof.

4. A process according to claim 1, wherein the displacement chromatography having the following steps:
 a) conditioning a chromatography column with a mobile phase;
 b) feeding the HMG-CoA reductase inhibitor dissolved in the mobile phase onto the chromatography column;
 c) introducing the displacer for displacing the HMG-CoA reductase inhibitor from the column; and
 d) obtaining the purified HMG-CoA reductase inhibitor.

5. A process according to claim 4, characterized in that the purified HMG-CoA reductase inhibitor is obtained by
 d1) collecting fractions; and
 d2) analyzing the fractions with analytical HPLC and pooling the fractions depending on the quality of purity.

6. A process according to claim 4, wherein the displacement chromatography further having:
 e) regenerating the chomatography column by washing the column with alcohol/water mixture to elute the displacer.

7. A process according to claim 4, wherein the mobile phase is selected from the group of solvents consisting of water, acetonitrile/water solutions, aqueous solutions of lower alcohols, and buffered dilute solutions of organic, halogenated organic or inorganic acids with alkaline metal cations, with ammonia or with amines.

8. A process according to claim 4, wherein the mobile phase is selected from the group of solvents consisting of water, acetonitrile/water solutions and aqueous solutions of lower alcohols.

9. A process according to claim 4, wherein the pH of the mobile phase used is between 4.5 and 10.5.

10. A process according to claim 9, wherein the pH of the mobile phase used is between 6.5 and 8.

11. A process according to claim 10, wherein the pH of the mobile phase used is 7.

12. A process according to claim 4, wherein the flow rate of the mobile phase through the chromatographic column is between 1.5 and 30 mL/(min cm$^2$).

13. A process according to claim 4, wherein the flow rate of the mobile phase/displacer mixture through the chromatographic column is between 3 and 15 ML/(min cm$^2$).

14. A process according to claim 6, wherein the stationary phase is regenerated with 20 to 100% aqueous solution of lower alcohols after completed chromatography.

15. A process according to claim 4, wherein the stationary phase is a reverse phase.

16. A process according to claim 15, wherein the stationary phase is a natural reverse phase including silica gel with alkyl chains of different lengths.

17. A process according to claim 15, wherein the stationary phase is either C–18 or C–8.

18. A process according to claim 15, wherein the stationary phase is a synthetic cross-linked polymer matrix.

19. A process according to claim 18, wherein the cross-linked polymer matrix is a copolymer of styrene and divinylbenzene.

20. A process according to claim 4, wherein the particle size of the stationary phase is between 3 and 20 μm.

21. A process according to claim 20, wherein the particle size of the stationary phase is between 7 and 15 μm.

22. A process according to claim 4, wherein the displacer is selected from the group consisting of long chain alcohols, long chain carboxylic acids, long chain alkyl ammonium salts, aromatic dicarboxylic acid esters, oxo- and dioxo-alcohols, polyalkylene polyglycol ethers and polyaryl or polyalkylene polyaryl ethers.

23. A process according to claim 4, wherein the concentration of the displacer in the mobile phase is between 1 and 35%.

24. A process according to claim 23, wherein the concentration of the displacer in the mobile phase is between 2 and 20%.

25. A process according to claim 4, wherein the HMG-CoA reductase inhibitor is selected from the group consisting of mevastatin, pravastatin, lovastatin, simvastatin, fluvastatin or atorvastatin.

26. A process according to claim 4, wherein the HMG-CoA reductase inhibitor has a lactone form or is in the form of the acid or the salt thereof.

* * * * *